(12) United States Patent
Avinash et al.

(10) Patent No.: US 7,627,160 B2
(45) Date of Patent: Dec. 1, 2009

(54) ANALYSIS OF TEMPORAL CHANGE USING DUAL OR MULTI-ENERGY DECOMPOSITION IMAGES

(75) Inventors: Gopal B. Avinash, New Berlin, WI (US); Kadri Nizar Jabri, Waukesha, WI (US); John M. Sabol, Sussex, WI (US); Renuka Uppaluri, Pewaukee, WI (US); Vianney Pierre Battle, Milwaukee, WI (US)

(73) Assignee: General Electric Company, Schnectady, NY (US)

( * ) Notice: Subject to any disclaimer, the term of this patent is extended or adjusted under 35 U.S.C. 154(b) by 1261 days.

(21) Appl. No.: 10/250,222

(22) Filed: Jun. 13, 2003

(65) Prior Publication Data

US 2004/0252873 A1 Dec. 16, 2004

(51) Int. Cl.
*G06K 9/00* (2006.01)
*H05G 1/70* (2006.01)
*H05G 1/10* (2006.01)
*A61B 5/05* (2006.01)

(52) U.S. Cl. .................. 382/132; 378/92; 378/101; 600/410

(58) Field of Classification Search .............. 382/128, 382/129, 130, 131, 132–134, 173; 600/407, 600/408, 410, 425; 128/922; 378/4, 15, 378/2, 21–27; 345/475, 691; 702/3, 6, 7; 707/100, 102, 200, 203
See application file for complete search history.

(56) References Cited

U.S. PATENT DOCUMENTS

| 4,542,459 | A  | * | 9/1985 | Riederer ..................... 600/431 |
| 6,559,641 | B2 | * | 5/2003 | Thesen ....................... 324/307 |
| 6,594,378 | B1 | * | 7/2003 | Li et al. ..................... 382/128 |
| 6,768,915 | B2 | * | 7/2004 | Brand et al. ................. 600/410 |
| 6,850,585 | B2 | * | 2/2005 | Hsieh et al. .................... 378/4 |
| 6,901,277 | B2 | * | 5/2005 | Kaufman et al. ............. 600/407 |
| 2003/0144589 | A1 | * | 7/2003 | Roell .......................... 600/410 |

* cited by examiner

Primary Examiner—Abolfazl Tabatabai
(74) Attorney, Agent, or Firm—Peter Vogel (57) ABSTRACT

An image processing system includes a dataset generator within an image controller generating a first derived member of a first dataset from an acquired member of the first dataset. The dataset generator further generates a first derived member of a second dataset from an acquired member of the second dataset. Temporal comparators within the image controller compare the first derived member of the first dataset and the first derived member the second dataset and generate a comparison signal therefrom.

21 Claims, 6 Drawing Sheets

ANALYSIS OF TEMPORAL CHANGE USING DUAL OR MULTI-ENERGY DECOMPOSITION IMAGES

BACKGROUND OF INVENTION

The present invention relates generally to imaging systems and more particularly to a temporal change method using dual or multi-energy decomposition images.

Imaging devices, such as X-ray machines, are widely used in both medical and industrial applications. Imaging devices often use temporal processing to track change in an object over time.

Temporal processing systems typically include the following general modules: acquisition storage module, segmentation module, registration module, comparison module, and reporting module. The input images are 1-D, 2-D, 3-D, derived, synthesized, or montaged, where multiple separate images from a single time point are combined to provide a larger composite, seamless image.

Detection of change in medical images of a patient, which are acquired at two different instances in time, has great potential for improving diagnosis. The advent of digital imaging allows computer-assisted detection and identification of these changes and the creation of a "dissimilarity image" containing the change information. This dissimilarity image can be read by a human controller or can become the input to an automated analysis device such as a CAD (computer assisted diagnosis) algorithm.

Temporal subtraction is a current temporal processing method wherein dissimilarity-images are calculated using a simple pixel-by-pixel subtraction of registered images. Simple subtraction, however, results in images with poor contrast, and is not substantially robust when the two initial images are acquired using different techniques.

For a temporal subtraction image, the resulting pixel values (and hence the displayed gray-levels) are proportional to the dissimilarity images acquired with temporal separation.

Input images are often registered and processed to compensate for several factors such as: the difference in positioning of the subject during the two image acquisitions, the difference in acquisition parameters, the difference in the bit resolution of the images, and the differences in any pre or post processing that may have been applied to the images.

Image comparison is a common task in a number of applications including temporal processing of mono-modality images (1-D, 2-D, 3-D, derived, synthesized, montaged). Current methods involve simple arithmetic operations conducted on these images, including subtraction or addition.

Another imaging method is dual-energy subtraction radiography, which includes the energy dependence of X-ray attenuation by different tissues. Energy subtraction is achieved through a rapid sequence of at least two exposures of different energy levels. Through the use of a decomposition algorithm, separate bone and soft tissue images are obtained.

Generally the following radiographs are generated from the aforementioned method: the standard (high energy) image, the low energy image, the soft tissue image, and the bone image. Individually, these images are useful for understanding spatial features in the soft tissue and bone, however they are not currently very useful for quantifying temporal changes.

The disadvantages associated with current, imaging systems have made it apparent that a new technique for quantifying temporal change is needed. The new technique should substantially increase the amount of information acquired from temporal processing. The present invention is directed to this end.

SUMMARY OF INVENTION

In accordance with one aspect of the present invention, an image processing system includes a dataset generator within an image controller generating a first derived member of a first dataset from two or more acquired members of the first dataset. The dataset generator further generates a first derived member of a second dataset from two or more acquired members of the second dataset. Temporal comparators within the image controller compare the first derived member of the first dataset and the first derived member of the second dataset and generate a comparison signal therefrom.

In accordance with another aspect of the present invention, an imaging method includes generating a first derived member of a first dataset, generating a first derived member of a second dataset, comparing a temporal change between the first derived member of the first dataset and the first derived member of the second dataset, and generating a temporal change image.

One advantage of the present invention is that it incorporates aspects of temporal imaging with multiple energy level imaging. Another advantage is that increased information is obtained through fewer imaging procedures.

Additional advantages and features of the present invention will become apparent from the description that follows and may be realized by the instrumentalities and combinations particularly pointed out in the appended claims, taken in conjunction with the accompanying drawings.

BRIEF DESCRIPTION OF DRAWINGS

For a more complete understanding of the invention, there will now be described some embodiments thereof, given by way of example, reference being made to the accompanying drawings, in which.

DETAILED DESCRIPTION

The present invention is illustrated with respect to an image processing system 10, particularly suited to the medical field. The present invention is, however, applicable to various other uses that may require temporal imaging, as will be understood by one skilled in the art.

Figure 1:
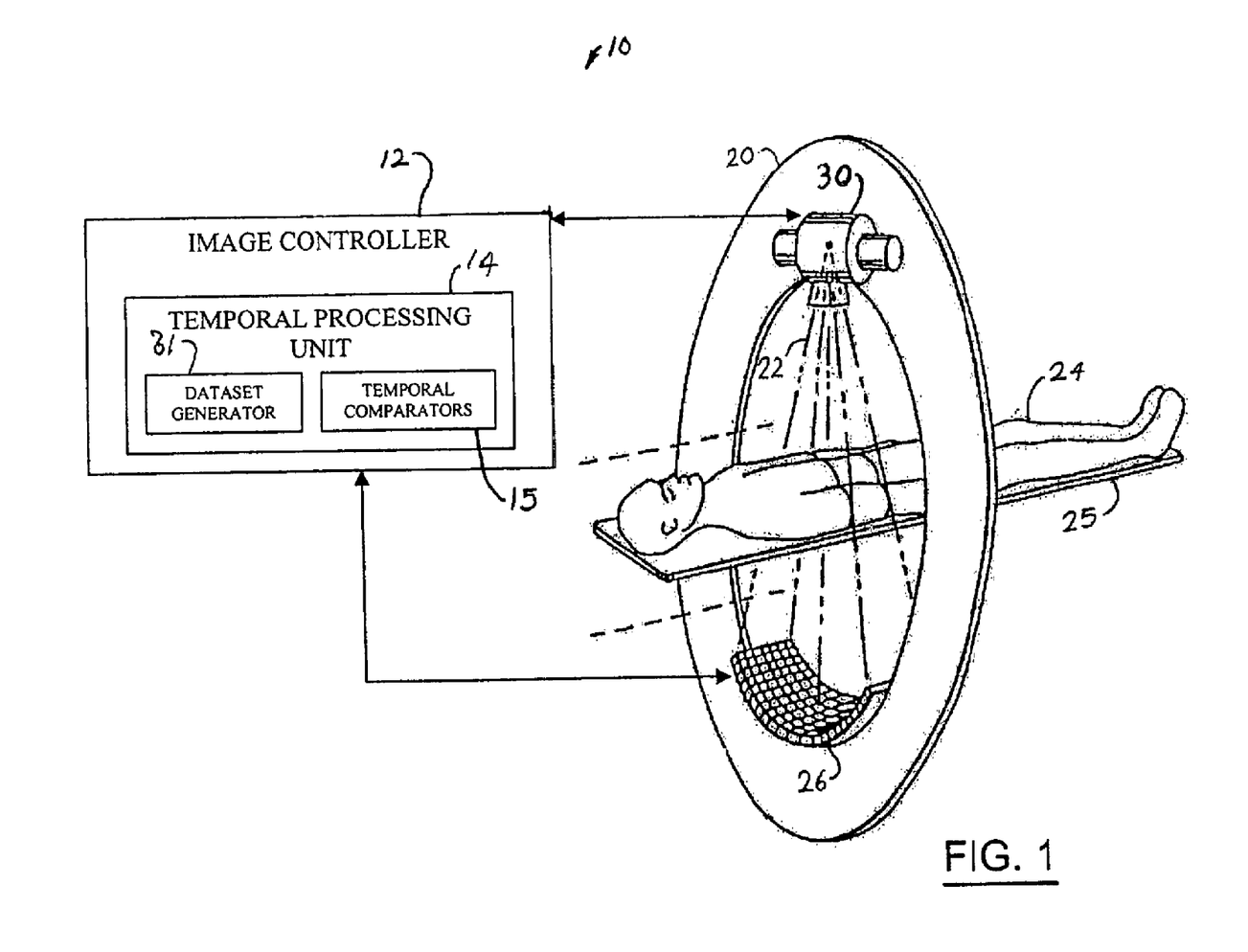
FIG. 1 is a diagram of an imaging system in accordance with an embodiment of the present invention.
Figure 2:
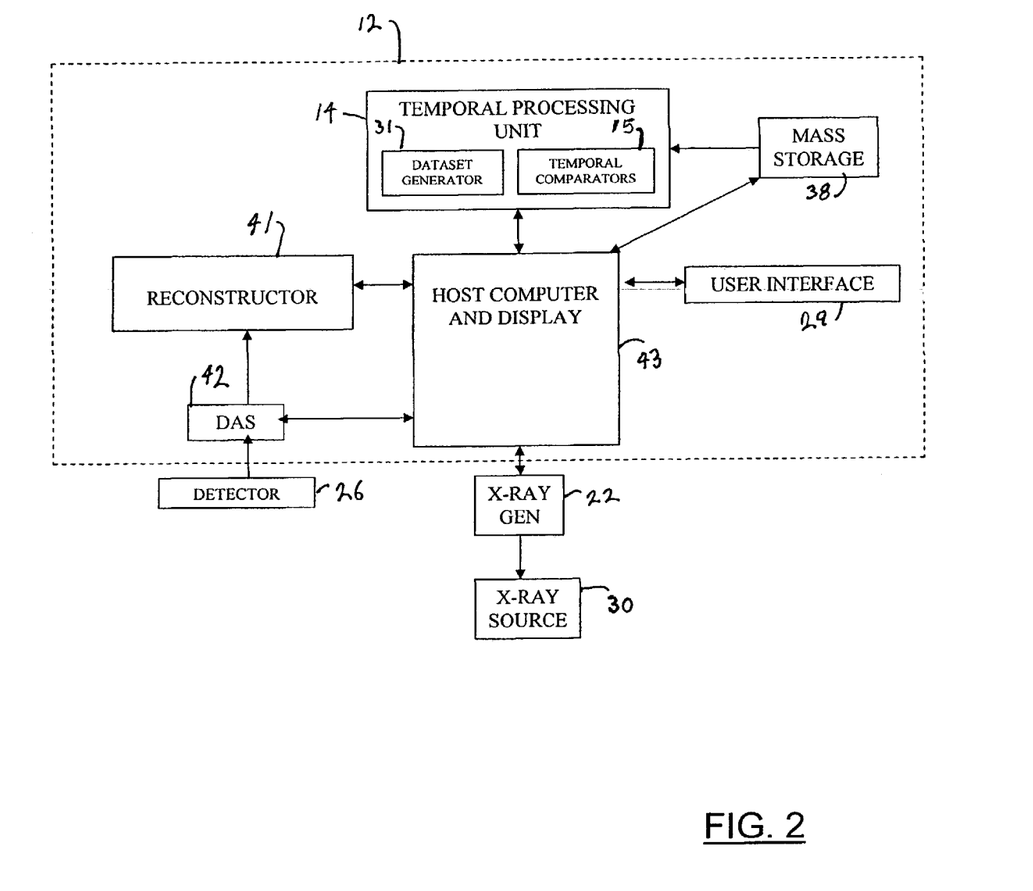
FIG. 2 is a partial schematic diagram of FIG. 1.

Referring to FIGS. 1 and 2, the image processing system 10 including an image controller 12 is illustrated. The image controller 12 includes a temporal processing unit 14 having a set of temporal comparators 15 and a dataset generator 31.

The image controller 12 also includes various other imaging components, such as a user interface 29, a mass storage 38, an image reconstructor 41, and a data acquisition system 42 (DAS), all of which couple to a host computer and display 43 and will be discussed later.

The image processing system 10 also includes an X-ray source 30 on a gantry-20 generating an X-ray flux 22 through an object 24 on a table 25. The system 10 further includes an x-ray detector 26, also coupled to the gantry 20, for receiving the X-ray flux 22 and generating detector signals.

For temporal change analysis, the image controller 12 receives the detector signals. The dataset generator 31 within the image controller 12 acquires acquired dataset members and generates derived dataset members. The temporal comparators 15 receive the dataset members and compare members of the different datasets. The image controller 12 then generates a temporal comparison image of at least two derived dataset members.

It is important to note is that for the present embodiment, a separate temporal comparator 15 may be included for each different energy level dataset member.

One embodiment of the temporal comparator 15 includes an acquisition storage module, a segmentation module, a registration module, a comparison module, and a report module.

The acquisition storage module within the temporal comparator 15 contains acquired high and low energy images and derived soft tissue and bone images received from the dataset generator 31.

The images sequenced by the acquisition storage module are 1-D, 2-D, 3-D, derived, synthesized, or montaged, such that multiple separate images from a single time point are combined to provide a larger composite, seamless image. One skilled in the art will realize that the acquisition storage module can include images from almost any digital imaging source (e.g. radiography, fluoroscopy, and computed tomography) capable of multiple energy imaging modes.

The segmentation module receives the images from the acquisition storage module and, through automated or manual operation in the user interface 29 or operator console 28, generates regions of interest between the X-ray images or dataset members. Often the entire image is the region of interest.

The registration module receives the region of interest signals from the segmentation module, provides methods of registration and therefrom generates a registration signal. If the regions of interest for temporal change analysis are small, rigid body registration transformations, including translation, rotation, magnification, and shearing, which are sufficient to register a pair of images from a first time ($t_1$) and a second time ($t_2$). If, however, the regions of interest are large, including almost the entire image, warped, elastic transformations are applied, as is the case in the preferred embodiment.

One way to implement the warped registration is to use a multi-scale, multi-region, pyramidal approach. For this approach, a different cost function highlighting changes is optimized at every scale. Such cost functions are correlation methods, such as mathematical correlation and sign-change measurement, or statistical methods such as entropy measurements and mutual information analysis.

For warped registration, images-are re-sampled at a given scale and subsequently divided into multiple regions. Shift vectors and contrast matchings are calculated for different regions. The images are then re-sampled and the warped registration process is repeated at the next higher scale until the pre-determined final scale is reached. In other situations, a combination of rigid registration and elastic is used, as is the case in the preferred embodiment.

The comparison module receives the segmentation signal and the registration signal and computes a dissimilarity measure between the registered images and therefrom generates a comparison signal. Registered image comparison is performed in several ways. In addition to, or instead of, using a simple subtraction between the registered images to obtain the dissimilarity image, the system includes an enhanced division method, which is described as $[S(t_1)*S(t_2)]/[S(t_2)*S(t_2)+1|]$ where the scalar constant $1|>0$.

The report module receives the comparison signal and provides the display and quantification capabilities for the user to visualize and or quantify the results of temporal comparison. Results of temporal comparisons are simultaneously displayed or overlaid on one another using a logical operator based on pre-specified criterion.

For quantitative comparison, color look-up tables for the overlaid images are used. The resultant image is alternately coupled with an automated pattern recognition technique to perform further qualitative and alternately manual or automated quantitative analysis of the research. The resulting-combination is realized with a multi-color overlay display.

The report module provides display and quantification capabilities for the user to visualize and/or quantify the results of temporal comparison. In practice, substantially all the available temporal image pairs are used for analysis.

Figure 3:
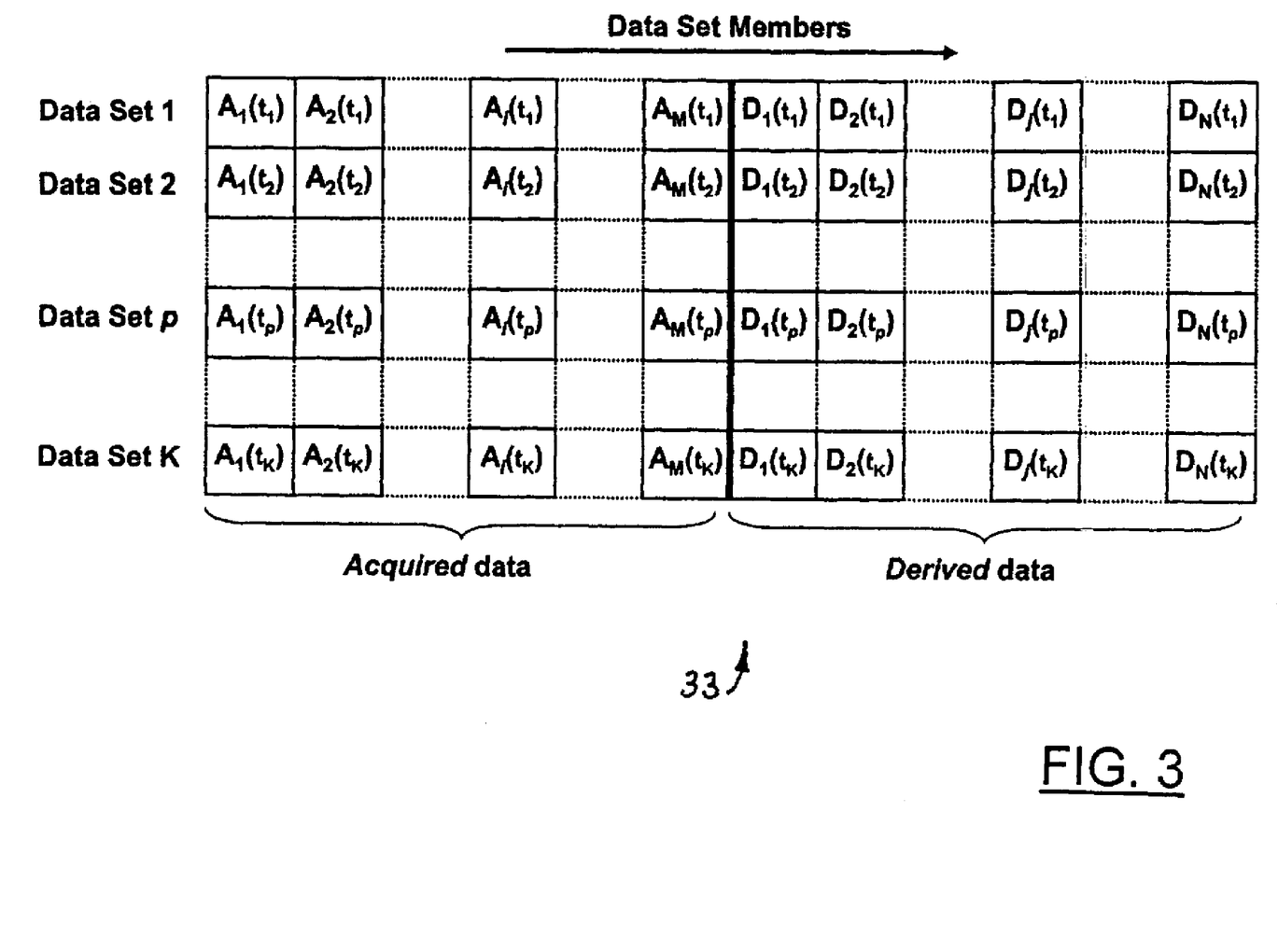
FIG. 3 is a chart of dataset member outputs for the dataset generator in accordance with another embodiment of the present invention.

Referring to FIG. 3, a chart 33 of dataset member outputs of the dataset generator 31 (see FIG. 2), in accordance with another embodiment of the present invention, is illustrated.

The dataset generator 31 generates datasets including members, which may be multidimensional images. These members can be acquired (A) or derived (D), and an individual dataset need not be complete (i.e. not all members available).

Acquired members from the acquisition storage module are retrieved by the dataset generator 31 from storage (e.g. the mass storage unit 38) corresponding to an earlier time point or from the image reconstructor 41, which receives signals from the DAS 42. Derived (decomposed) members result from the combination of existing members (acquired or derived), including those acquired or derived in the past. Acquired and Derived members at two different times are not necessarily of the same number or of the same type.

The dataset generator 31 is adapted for either dual-energy imaging or in alternate embodiments, multi-energy imaging. For the dual-energy case, H, B, S, or L datasets are generated at two time points $t_1$ and $t_2$. H corresponds to high energy, L corresponds to low energy, S corresponds to soft tissue, and B corresponds to bone.

The present embodiment is illustrated with only four energy levels, H, S, B, and L, it is to be understood, however, that the general multi-energy approach of the present invention includes any number of images in the acquisition and temporal sequences.

To clarify, the illustrated output of the dataset generator includes $H_1(t_1)$ represented by the general case of $A_1(t_1)$. The dataset generator, however, in alternate embodiments generates a virtually unlimited number of dataset members, for example, acquired data e.g. $A_1(t_1), A_2(t_1),$ and $A_i(t_i)$ to $A_M(t_1)$ and $A_1(t_2)$ and $A_1(t_p)$ to $A_1(t_k)$. M signifies the number of energy level images, and K indicates the number of temporal images are taken, as will be understood by one skilled in the art.

For derived dataset members, $D_1(t_1)$ is $L(t_1)$ for the dual-energy case or another derived member energy level known in the art for the multi-image case. Important to note is that the multi-image case includes members up to $D_N(t_K)$, which includes almost any number of energy levels up to N for up to K temporal changes.

Figure 4:
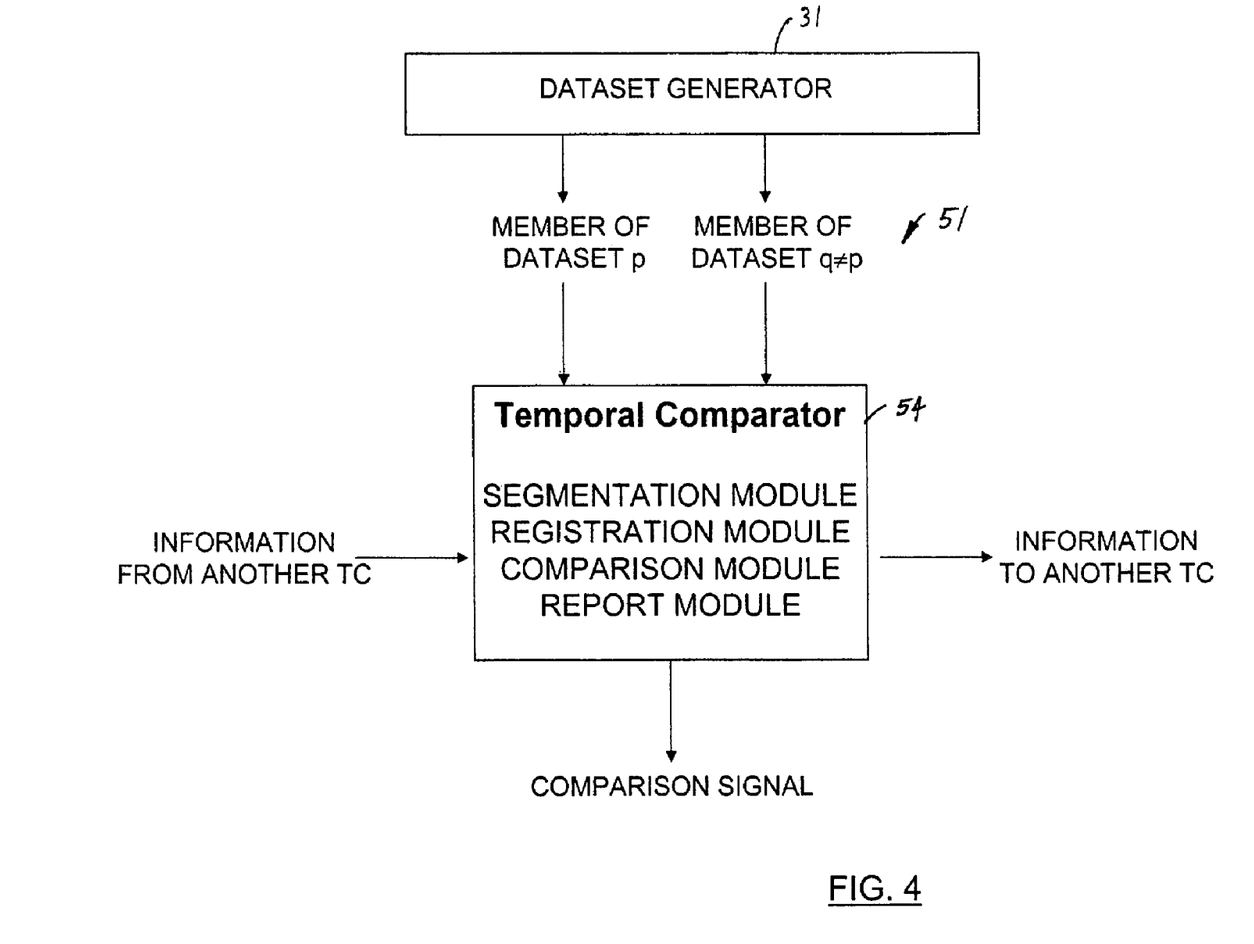
FIG. 4 is a block diagram of a temporal comparator system in accordance with another embodiment of the present invention.

Referring to FIG. 4, a block diagram of a general temporal comparator system 51, in accordance with another embodiment of the present invention, is illustrated. The dataset generator 31 generates a member of dataset p and a member of some other dataset. These signals are received in the temporal comparator 54. The temporal comparator generates a comparison signal based on two dataset members acquired or derived at different times. The temporal comparator 54 also receives and shares signals with other temporal comparators to maximize efficiency and generate the comparison signal.

Figure 5:
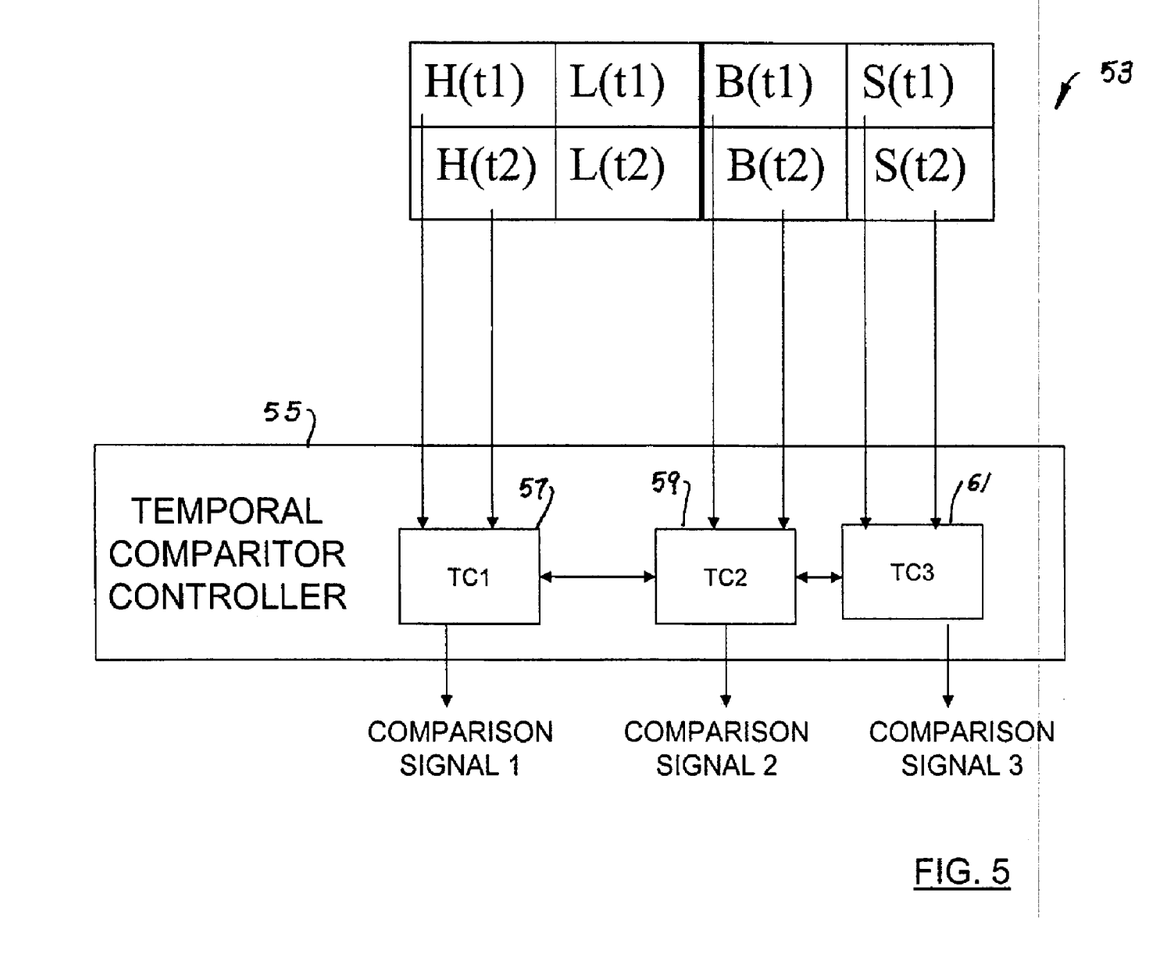
FIG. 5 is a block diagram of a dual imaging system in accordance with another embodiment of the present invention.

FIG. 5 illustrates a temporal comparison 53 of various temporal pairs. The dual-energy case is illustrated; however, the present invention also includes embodiments for multi-energy systems, as was previously discussed.

For dual-energy systems, images from the dataset generator 31 are received in the temporal comparator controller 55, which is a subsection of the temporal processing unit 14. The temporal comparator controller 55 includes several (up to four for the dual-energy case) temporal comparators 57, 59, 61, which each include a segmentation module, a registration module, a comparison module and a report module.

Each of the temporal comparators 57, 59, 61 share data with the other temporal comparators and generate comparison signals in response to the shared data and the dual-energy data. In other words, the temporal comparator controller 55 contains the architecture of the comparison system. It defines how each individual temporal comparator taps in the dataset and how these are interconnected.

Figure 6:
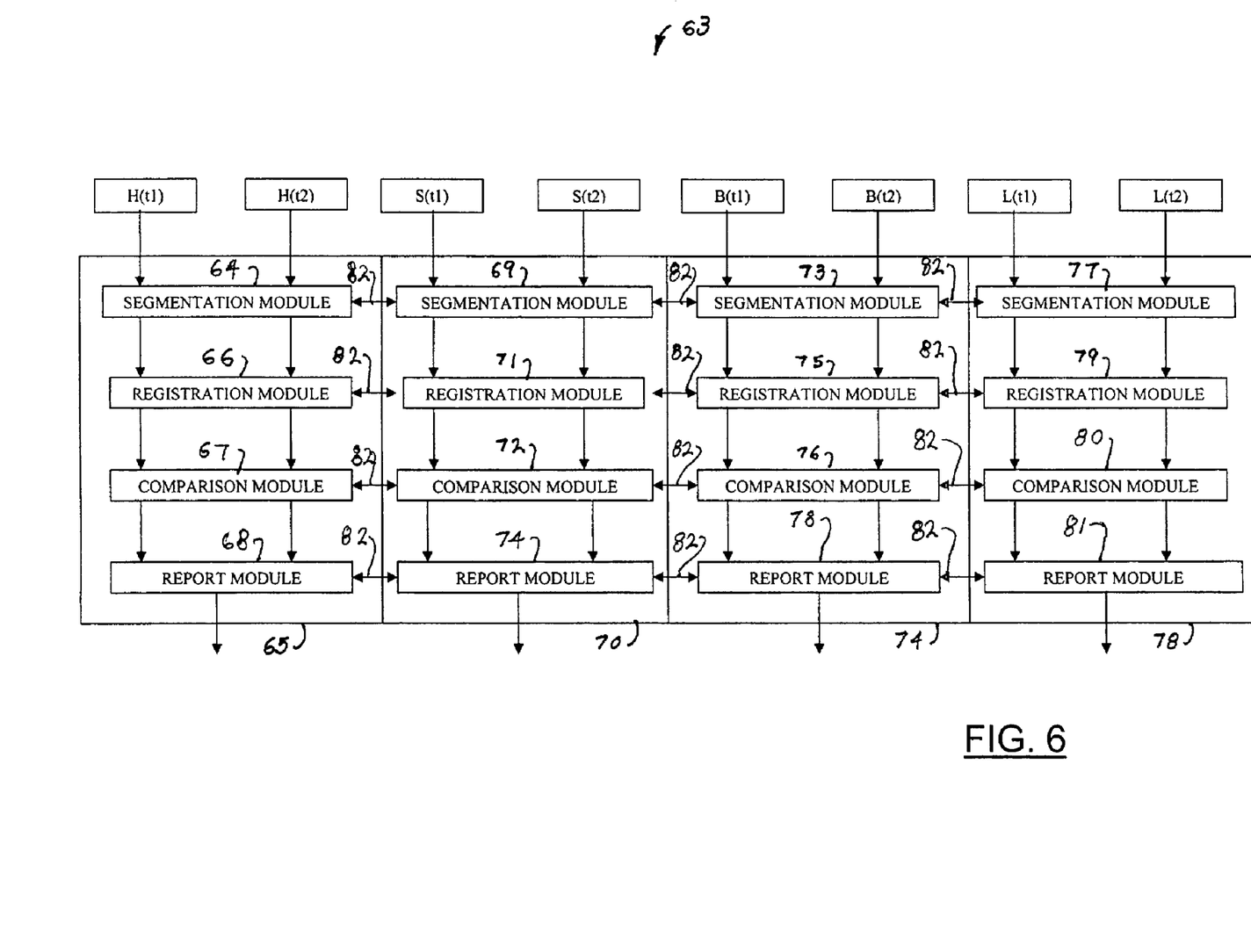
FIG. 6 is a block diagram of the parallel sections of a temporal comparison controller corresponding to various temporal pairs in accordance with another embodiment of the present invention.

Referring to FIG. 6, a block diagram 63 of the parallel sections of a temporal comparison controller corresponding to various temporal pairs, in accordance with another embodiment of the present invention, is illustrated. The images $H(t_1)$ and $H(t_2)$ are received in a first segmentation module 64 of the first temporal comparator 65 from the dataset generator 31. A first registration module 66 receives the first segmentation module signal, a first comparison module 67 receives the first registration signal, and a first report module 68 receives the first comparison signal. One skilled in the art will realize that the dual-energy example is not meant to be limiting and multi-energy systems are also included.

The images $S(t_1)$ and $S(t_2)$ are illustrated received in a second segmentation module 69 of a second temporal comparator 70. A second registration module 71 receives the second segmentation module signal, a second comparison module 72 receives the second registration signal, and a second report module 74 receives the second comparison signal.

The images $B(t_1)$ and $B(t_2)$ are illustrated received in a third segmentation module 73 of a third temporal comparator 74. A third registration module 75 receives the third segmentation module signal, a third comparison module 76 receives the third registration signal, and a third report module 78 receives the third comparison signal.

The images $L(t_1)$ and $L(t_2)$ are illustrated received in a fourth segmentation module 77 of a fourth temporal comparator 78. A fourth registration module 79 receives the fourth segmentation module signal, a fourth comparison module 80 receives the fourth registration signal, and a fourth report module 78 receives the fourth comparison signal. It is to be understood that the system includes any number of temporal comparators coupled together in parallel.

Shift vector information 82 is shared between any of the segmentation, registration, comparison or report modules. The shift vectors either connect from consecutive parallel modules or multiple modules in tandem. Therefore, information acquired in one module can be used to share or refine other sections among the various image or dataset pairs.

In operation, an imaging method includes generating a first acquired member of a first dataset and generating a first acquired member of a second dataset. A first derived member of the first dataset is generated and a first derived member of the second dataset is generated. A temporal change is analyzed between the first acquired member of the first dataset and the first acquired member of the second dataset and a temporal change image is generated. One skilled in the art will realize that this method may be extended to include numerous members and temporal image modules in communication.

The following is an example of a dual-energy temporal analysis reporting method for lung cancer chest imaging in accordance with one embodiment of the present invention. To begin with, a dual-energy exam is conducted on a patient and is then processed with a temporal analysis system.

A temporal analysis identifies two notable lesions characteristic of malignancy on the soft tissue image. On the bone image, a temporal analysis operation within the temporal comparator identifies a calcified nodule indicating a benign process and a bone lesion. The temporal analysis continues taking a second dual-energy exam of the aforementioned identified sections.

During the synthesis stage, the overlay of these results indicates that one of the soft tissue nodules is the same as the calcified nodule apparent on the bone image. The reviewer is then presented with a high-energy image acquired through a technique similar to standard practice for single energy chest radiography. The reviewer is also presented with the same image with markers indicating the results of the temporal analysis operations superimposed on the image data. This second image is simultaneously displayed on a second hard or soft copy image display, or toggled with the other images via software on a soft copy display. The second image is alternately superimposed with different markers for different suspicious regions.

From the foregoing, it can be seen that there has been brought to the art a new image processing system 10. It is to be understood that the preceding description of the preferred embodiment is merely illustrative of some of the many specific embodiments that represent applications of the principles of the present invention. Numerous and other arrangements would be evident to those skilled in the art without departing from the scope of the invention as defined by the following claims.

The invention claimed is:

1. An image processing system comprising:
   a medical imaging assembly comprising:
   an image source;
   an imaging detector generating datasets in response to said imaging source; and
   a temporal processing unit in communication with said imaging detector and adapted to generate a first derived member of a first dataset from two or more acquired members of said first dataset;
   said temporal processing unit further adapted to generate a first derived member of a second dataset from two or more acquired members of said second dataset, said temporal processing unit further adapted to compare said first derived member of said first dataset and said first derived member of said second dataset and generate a comparison signal therefrom.

2. The image processing system of claim 1 wherein said acquired members of said first dataset and said first derived member of said first dataset are at least one of dual-energy or multiple energy decomposition images.

3. The image processing system of claim 1 wherein said first derived member is one of a one-dimensional image, a two-dimensional image, a three-dimensional image, a one-dimensional montage image, a two-dimensional montage image, or a three-dimensional montage image.

4. The image processing system of claim 1 wherein said temporal processing unit comprises a dataset generator and a first temporal comparator,
wherein said dataset generator is adapted to generate said first derived member of said first dataset and said first derived member of said second dataset, and
wherein said first temporal comparator is adapted to receive said first derived member of said first dataset and said first derived member of said second dataset and generate said comparison signal therefrom.

5. The image processing system of claim 1 wherein said temporal processing unit comprises a dataset generator, a first temporal comparator and a second temporal comparator,
wherein aid dataset generator is adapted to generate said first derived member of said first dataset and said first derived ember of said second dataset,
wherein said first temporal comparator is adapted to receive said first derived member of said first dataset; and
wherein said second temporal comparator is adapted to receive said first derived member of said second dataset.

6. The image processing system of claim 5 wherein an information transfer is refined between said first temporal comparator and said second temporal comparator and wherein said information transfer includes at least one of a shift vector or a contrast matching.

7. The image processing system of claim 1 wherein said temporal processing unit is adapted to generate said acquired member of said first dataset including at least two different energy images, and
wherein said temporal processing unit is adapted to generate said first derived member of said first dataset including at least one of a soft tissue image or a bone image.

8. The image processing system of claim 1 wherein said temporal processing unit is further adapted to generate a first derived member of a third dataset from an acquired member of said third dataset.

9. The image processing system of claim 1 wherein said temporal processing unit is further adapted to generate a temporal change image from said comparison signal and display said temporal change image, wherein displaying said temporal change image further includes at least one of:
displaying said temporal change image with a first marker indicating a result of a temporal analysis operation superimposed on a image data, simultaneously displaying said temporal change image on a second hard or soft copy image display or toggling said temporal change image with at least one other image via software on a soft copy display, or superimposing said temporal change image with different markers for different suspicious regions.

10. An imaging method comprising:
generating a first dataset by passing a medical imaging source through a patient into an imaging detector, said imaging detector generating said first dataset;
generating a second dataset by passing said medical imaging source through the patient into said imaging detector;
processing said first and second data sets using a temporal processor configured to;
generating a first derived member of said first dataset;
generating a first derived member of said second dataset;
comparing a temporal change between said first derived member of said first dataset and said first derived member of said second dataset; and
generating a temporal change image.

11. The imaging method of claim 10 further comprising sharing information between a first temporal comparator and a second temporal comparator.

12. The imaging method of claim 11 wherein sharing information includes sharing at least one of a shift vector or an information contrast matching.

13. The imaging method of claim 10 further comprising sharing a plurality of shift vectors between a plurality of registration modules.

14. The imaging method of claim 10 further comprising displaying said temporal change image.

15. The imaging method of claim 10 wherein generating said temporal change image further comprises generating a dataset including a one-dimensional image, a two-dimensional image, a three-dimensional image, a one-dimensional montage image, a two-dimensional montage image, or a three dimensional montage image.

16. The image method of claim 10 further comprising:
displaying said temporal change image, wherein displaying and temporal change image further comprises at least one of:
displaying said temporal change image with a first marker indicating a result of a temporal analysis operation superimposed on an image data, simultaneously displaying said temporal change image on a second hard or soft copy image display or toggling said temporal change image with at least one other image via software on a soft copy display, or superimposing said temporal change image with different markers for different suspicious regions.

17. An imaging method comprising:
generating a first dataset by passing a medical imaging source through a patient into an imaging detector, said imaging detector generating said first dataset;
generating a second dataset by passing said medical imaging source through the patient into said imaging detector;
processing said first and second data sets using a temporal processor configured to;
generating a first derived member of said first dataset;
generating a first derived member of said second dataset;
comparing said first derived member of said first dataset and said first derived member of said second dataset; and
generating a temporal change image.

18. The imaging method of claim 17 wherein generating said first derived image if said first dataset further comprises generating at least one of a bone image or a soft tissue imaging.

19. The imaging method of claim 17 further comprising generating a number of derived members from multiple energy levels.

20. The imaging method of claim 17 further comprising:
displaying said temporal change image, wherein displaying said temporal change image further comprises at least one of:
displaying said temporal change image with a first marker indicating a result of a temporal analysis operation superimposed on an image data, simultaneously displaying said temporal change image on a second hard or soft copy image display or toggling said temporal change image with at least one other image via software on a soft copy display, or superimposing said temporal change image with different markers for different suspicious regions.

21. The imaging method of claim 20 wherein displaying said temporal change image comprises displaying said temporal change image and a current image on at least one color overlay.

\* \* \* \* \*

UNITED STATES PATENT AND TRADEMARK OFFICE
CERTIFICATE OF CORRECTION

PATENT NO. : 7,627,160 B2
APPLICATION NO. : 10/250222
DATED : December 1, 2009
INVENTOR(S) : Avinash et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1527 days.

Signed and Sealed this

Second Day of November, 2010

David J. Kappos
*Director of the United States Patent and Trademark Office*